United States Patent
Iyunni

(10) Patent No.: US 11,369,547 B2
(45) Date of Patent: Jun. 28, 2022

(54) CATHETER WITH BALLOON VALVE

(71) Applicant: SaiNath Intellectual Properties, LLC, Pinellas Park, FL (US)

(72) Inventor: Venkata Sesha Sayi Nath Iyunni, Pinellas Park, FL (US)

(73) Assignee: SaiNath Intelleotual Properties, LLC, Pinellas Park, FL (US)

( * ) Notice: Subject to any disclaimer, the term of this patent is extended or adjusted under 35 U.S.C. 154(b) by 88 days.

(21) Appl. No.: 16/463,044

(22) PCT Filed: Dec. 28, 2018

(86) PCT No.: PCT/US2018/067923
§ 371 (c)(1),
(2) Date: May 22, 2019

(87) PCT Pub. No.: WO2020/139378
PCT Pub. Date: Jul. 2, 2020

(65) Prior Publication Data
US 2020/0297585 A1    Sep. 24, 2020

(51) Int. Cl.
*A61J 15/00* (2006.01)
*A61M 25/00* (2006.01)

(52) U.S. Cl.
CPC ....... *A61J 15/0042* (2013.01); *A61J 15/0015* (2013.01); *A61M 25/0068* (2013.01)

(58) Field of Classification Search
CPC ............. A61J 15/0003; A61J 15/0015; A61J 15/0042; A61J 15/0049; A61J 15/0069; A61J 15/0073; A61J 15/0092; A61M 1/0084; A61M 3/0295; A61M 25/0026; A61M 25/0068; A61M 2025/0019; A61M 16/0454; A61M 16/0456; A61M 16/0459; A61M 25/0075; A61M 2025/0076; A61M 2025/0078; A61M 2025/0079; A61M 2025/1006; A61M 2025/1013; A61M 2025/1065; A61M 39/22; A61M 39/227; A61M 39/228; A61M 2039/242;
(Continued)

(56) References Cited

U.S. PATENT DOCUMENTS 4,166,468 A * 9/1979 Haynie ............. A61M 16/0409
                                                    128/207.15
4,248,221 A * 2/1981 Winnard ........... A61M 16/0404
                                                    128/207.15
(Continued)

FOREIGN PATENT DOCUMENTS

DE    3035243 A1    3/1982
EP    2599509 A2    6/2013
WO    2017079061 A2   5/2017

OTHER PUBLICATIONS

International Search Report and Written Opinion of PCT/US2018/067923.
(Continued)

*Primary Examiner* — Amber R Stiles
*Assistant Examiner* — Avery Smale
(74) *Attorney, Agent, or Firm* — Carlton Fields, PA; Eleanor M. Yost

(57) ABSTRACT

A catheter having a selectively inflatable external balloon and an internal balloon, where the internal balloon is operable as a valve to control fluid flow through a channel.

15 Claims, 11 Drawing Sheets

(58) Field of Classification Search
CPC ...... A61M 2039/2433; A61M 25/1006; A61M 25/10; A61M 25/1011; A61M 2025/1015
See application file for complete search history.

(56) References Cited

U.S. PATENT DOCUMENTS

| | | | |
|---|---|---|---|
| 4,771,782 A * | 9/1988 | Millar | A61B 5/14539 |
| | | | 600/486 |
| 5,624,395 A | 4/1997 | Mikhail et al. | |
| 6,582,395 B1 * | 6/2003 | Burkett | A61M 25/04 |
| | | | 604/910 |
| 7,396,351 B2 * | 7/2008 | Freyman | A61M 25/00 |
| | | | 604/537 |
| 9,283,151 B2 * | 3/2016 | Porreca, Jr. | A61J 15/0069 |
| 2007/0250104 A1 | 10/2007 | Condrea et al. | |
| 2014/0180252 A1 | 6/2014 | Gabriel | |
| 2014/0276663 A1 | 9/2014 | Pinchuk et al. | |

OTHER PUBLICATIONS

EP Application 18887214.7 Supplementary European Search Report dated Feb. 19, 2020.
International Search Report and Written Opinion of PCT/US2018/067923, dated Dec. 28, 2018.

* cited by examiner

CATHETER WITH BALLOON VALVE

CROSS REFERENCE TO RELATED APPLICATIONS

This application is a U.S. national stage application under 35 USC § 371 of International Patent Application No. PCT/US18/67923, filed Dec. 28, 2018, the entire contents of which are incorporated herein by reference.

FIELD OF THE INVENTION

The present disclosure relates to medical devices, and in particular, to catheters and catheter assemblies, including catheters used for percutaneous feeding, drainage, and dilation of various strictures.

BACKGROUND OF THE INVENTION

Gastrostomy feeding devices provide access to the stomach at a stoma site. Such ports are typically left in place over a prolonged period of time and are used for feeding and medicating a patient. With some exceptions within individual designs, gastrostomy tubes or tube assemblies generally include several common features: (a) a tube to carry feeding formula into the stomach and/or the intestine, (b) an outflow port in the distal end of the tube, which may be incorporated in the end or the side wall of the tube, or in a separate, molded bolus fastened to the distal end of the tube, (c) an administration set connector attached to the proximal end of the tube, which is outside of the patient, (d) a distal end device to hold the tube in the stomach, e.g., an inflatable balloon or soft disc as described in U.S. Pat. No. 5,071,405, (e) an external bolster to secure the tube at the point where it exits the skin, and (f) a valve to, e.g., prevent leakage of gastric acids from the patient such as when the administration set is being changed or when coughing causes excessive back pressure.

Anti-reflux valves, for example, are one-way valves that prevent the reflux of gastric contents because the leakage of gastric contents, which are highly acidic, can cause severe skin burns or tissue maceration leading to chronic skin infections. Valves that have been used in prior art gastrostomy feeding devices, however, do not always work as intended to prevent reflux, particularly after many repeated uses. Existing anti-reflux valves include flapper valves that often clog and malfunction, as detailed in U.S. Pat. No. 5,865,816. Other known valve structures include slit or membrane valves, as detailed in U.S. Pat. No. 4,351,328, and the hemostasis valve of U.S. Pat. No. 5,000,745. A membrane valve, for example, incorporates one or more membranes that seal under the influence of the material's own resiliency. These membrane structures, however, tend to become stretched by repeated use, causing the valves to lose their ability to positively seal closed and leakage will begin to occur. These valve structures would not prove to be reliable over long term and repeated use. Other medical devices have included valve structures that apply compressive force in some form against the valve opening to bias the valve towards a closed position. Such valves cannot generally be used to control both inflow and out-flow of fluids in the device.

The location of such valves is also important. It is often necessary to open a valve to decompress a cavity, so a valve that is easily accessible and operable is desirable. Some gastrostomy valves are positioned so that special decompression sets are required to activate them if feeding is not taking place.

Just as gastrostomy tubes or tube assemblies are used for enteral feeding, so other catheter tubes or tube assemblies are used to, for example, administer drugs to a human body, or drain urine from the bladder. Rather than operate to administer a fluid to the body, some operate to withdraw or release fluid from the body. Such tubes or tube assemblies comprise the same general features or components, as would be apparent to one of ordinary skill in the art.

There is a need for a new catheter with an internal valve that provides a positive sealing effect over the course of many recurrent uses of the valve and over an extended period of time if left in place on or in a patient. Further, a valve that is operable to control inflow and outflow is also desirable. Such a device would eliminate the need for, e.g., external valves and closure caps on inlets, which will lessen the risk of dripping (e.g., in the case of medication), backflow, spillage, and reflux. Such devices would be both safer and more convenient to use than devices that have been provided in the past.

SUMMARY OF THE INVENTION

Catheters are known that use inflatable balloons as bolsters or seals, such as U.S. Pat. No. 4,701,163 and the like, to prevent the catheter from being dislodged from a cavity and sealing off a stoma, such as for gastrointestinal feeding. Other catheters, such as U.S. Pat. No. 4,796,629, use balloons to dilate blood vessels and the like. However, these dilation balloons are very different from balloons inflated to secure feeding tubes. For example, a balloon inflated to secure a feeding tube is inflated and remains inflated for an extended time, until the catheter is removed. The balloon for dilation is inflated only for a short period of time to dilate a lumen or for expanding a stent or the like. None of these devices, however, simultaneously use a balloon as a valve.

To address these and other general aspects, one embodiment of the invention disclosed herein includes a catheter including: a proximal end and a distal end opposite the proximal end; a port housing disposed near the proximal end having a main inlet port fluidically coupled to a main fluid flow channel having a flow channel wall, and two or more fluid inlet port housings each fluidically coupled to a fluid flow channel; a cylindrical shaft having an outer surface wall enclosing the fluid flow channel(s); a fitting connecting the port housing to the cylindrical shaft; where the main fluid flow channel extends longitudinally through the cylindrical shaft from the proximal end to the distal end of the catheter; where the two or more fluid inlet port housings each further include a fluid inlet port for receiving and channeling a fluid; where each fluid flow channel is disposed within and extends longitudinally through the cylindrical shaft, and terminates at a balloon inflation port fluidically coupled to a balloon inflation orifice operable to channel fluid into a balloon; a selectively inflatable external balloon secured to and engirdling a portion of the outer surface wall of the cylindrical shaft and enclosing at least one balloon inflation orifice, where the selectively inflatable external balloon is fluidically coupled to at least one balloon inflation port, fluid flow channel, and fluid inlet; an internal balloon valve disposed inside the cylindrical shaft, engirdling a portion of the flow channel wall of the main fluid flow channel and enclosing at least one balloon inflation orifice, where the internal balloon valve is fluidically coupled to at least one balloon inflation port, fluid flow channel, and fluid inlet;

where the internal balloon valve, when inflated, distends a portion of the flow channel wall inwardly such that fluid flow through the main fluid flow channel is restricted except for fluids introduced to main inlet port under pressure; and an outlet port disposed at the distal end fluidically coupled to the main fluid flow channel.

Another embodiment includes a catheter including: a proximal end and a distal end opposite the proximal end; a port housing disposed near the proximal end having a main inlet port fluidically coupled to a main fluid flow channel having a flow channel wall, and two or more fluid inlet port housings each fluidically coupled to a fluid flow channel; a cylindrical shaft having an outer surface wall enclosing the fluid flow channel(s); a fitting connecting the port housing to the cylindrical shaft; where the main fluid flow channel extends longitudinally through the cylindrical shaft from the proximal end to the distal end of the catheter; where the two or more fluid inlet port housings each further include a fluid inlet port for receiving and channeling a fluid; where each fluid flow channel is disposed within and extends longitudinally through the cylindrical shaft, and terminates at a balloon inflation port fluidically coupled to a balloon inflation orifice operable to channel fluid into a balloon; a selectively inflatable external balloon secured to and engirdling a portion of the outer surface wall of the cylindrical shaft and enclosing at least one balloon inflation orifice, where the selectively inflatable external balloon is fluidically coupled to at least one balloon inflation port, fluid flow channel, and fluid inlet; a selectively inflatable middle balloon disposed within the selectively inflatable external balloon and secured to and engirdling a portion of the outer surface wall of the cylindrical shaft and enclosing at least one balloon inflation orifice, where the selectively inflatable middle balloon is fluidically coupled to at least one balloon inflation port, fluid flow channel, and fluid inlet; an internal balloon valve disposed inside the cylindrical shaft, engirdling a portion of the flow channel wall of the main fluid flow channel; where the selectively inflatable middle balloon, when inflated, exerts pressure on the internal balloon valve to restrict fluid flow through the main fluid flow channel except for fluids introduced to main inlet port under pressure; and an outlet port disposed at the distal end fluidically coupled to the main fluid flow channel.

In yet another embodiment, the invention includes a method of operating a catheter having an internal balloon valve, comprising the steps of inflating a selectively inflatable external balloon secured to and engirdling a portion of an outer surface wall of a cylindrical shaft of a catheter by introducing a fluid to a first fluid inlet port disposed within a first fluid inlet port housing located at a proximal end of the catheter, channeling the fluid from the first fluid inlet port through a first fluid flow channel disposed within and extending longitudinally through the cylindrical shaft of the catheter to fill the selectively inflatable external balloon, wherein the first fluid flow channel is fluidically coupled to a first balloon inflation port fluidically coupled to the selectively inflatable external balloon; and inflating an internal balloon valve disposed inside the cylindrical shaft of the catheter, wherein the internal balloon valve engirdles a main fluid flow channel disposed within and extending longitudinally through the cylindrical shaft of the catheter by introducing a second fluid to a second fluid inlet port disposed within a second fluid inlet port housing located at a proximal end of the catheter, channeling the second fluid from the second fluid inlet port through a second fluid flow channel disposed within and extending longitudinally through the cylindrical shaft of the catheter to fill the internal balloon valve, wherein the second fluid flow channel is fluidically coupled to a second balloon inflation port fluidically coupled to the internal balloon valve, and distending a surface of the main flow channel such that fluid flow through the main fluid flow channel is restricted.

BRIEF DESCRIPTION OF THE DRAWINGS

The present invention is disclosed with reference to the accompanying drawings, wherein.

Corresponding reference characters indicate corresponding parts throughout the several views. The examples set out herein illustrate several embodiments of the invention but should not be construed as limiting the scope of the invention in any manner.

DETAILED DESCRIPTION

Figure 1:
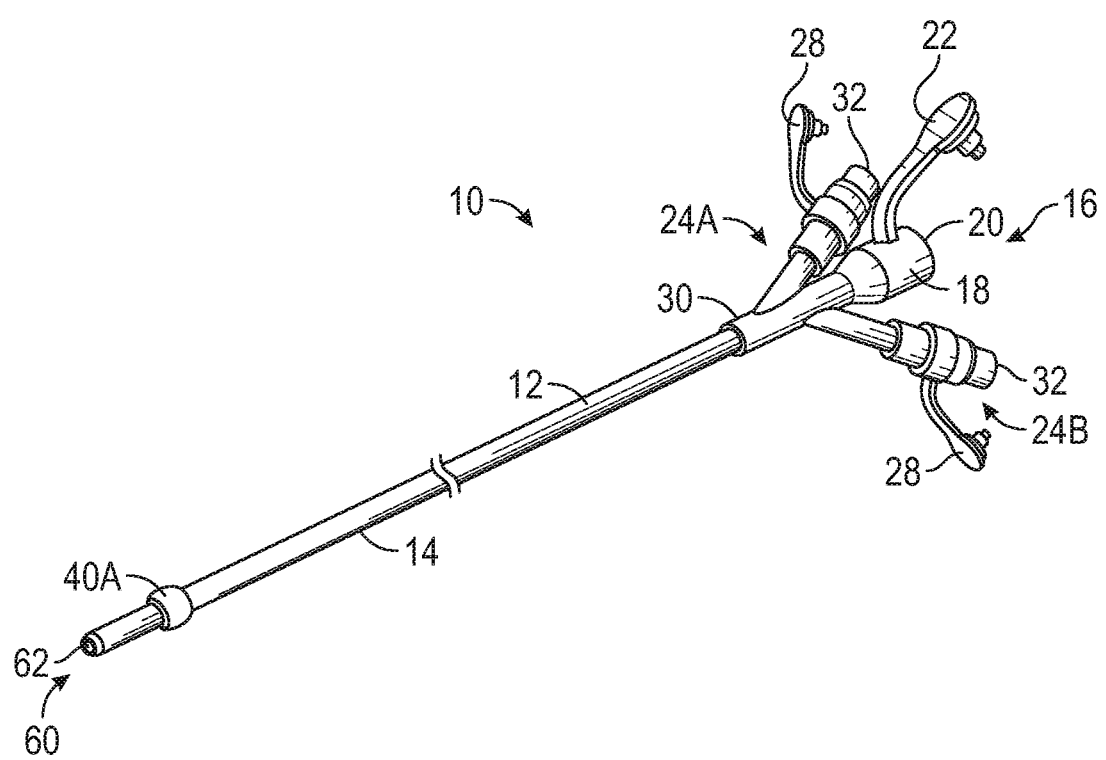
FIG. 1 is a schematic example of a catheter having a selectively inflatable external balloon operable as a bolster and an internal balloon valve.

In FIG. 1, a catheter 10 is shown. Catheter 10 comprises shaft 12, which may be a stiff or flexible cylindrical tubular member or other desirable shape, having an outer surface wall 14. Shaft 12 encloses a plurality of fluid flow channels or lumens, such as those shown in FIG. 2. Shaft 12 may be fabricated from medical grade silicone or plastic or other suitable material known in the art. The circumference of shaft 12 may be, e.g., from 5 French to 24 French, and the length may be any suitable length for the intended purpose of the catheter. For example, in connection with a percutaneous endoscopic gastrostomy apparatus, shaft 12 may be about 2 cm to about 37 cm in length. Alternatively, in connection with a colostomy tube apparatus, shaft 12 may be about 2 cm to about 37 cm in length.

Figure 2:
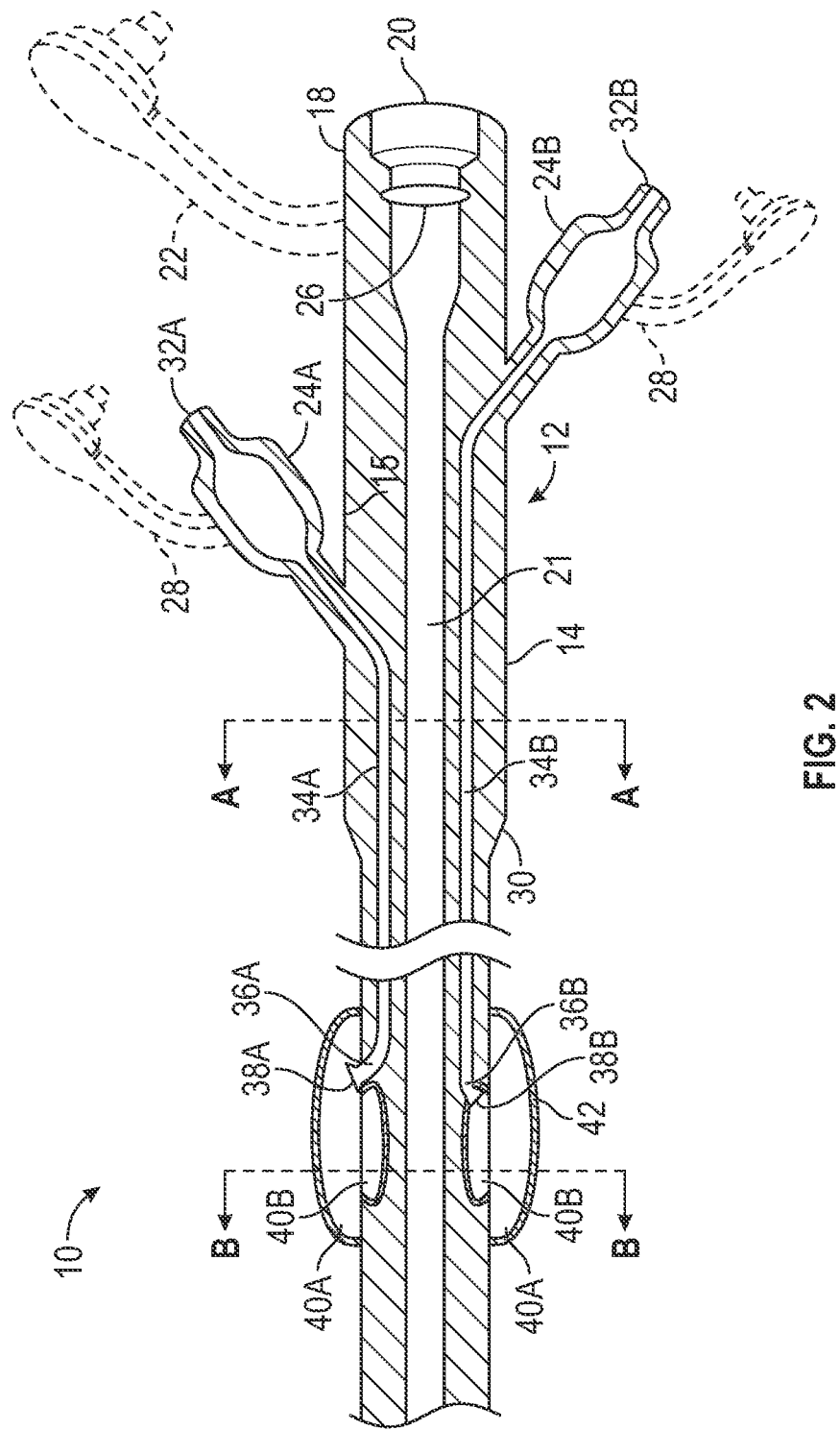
FIG. 2 is a cross-sectional view of the catheter of FIG. 1.

Catheter 10 further comprises a proximal end 16, a distal end 60, outlet port 62 (which may have an aperture or opening for releasing content like food from main fluid flow channel 21 and be subject to back-flow or reflux from a stomach or other cavity), and port housing 18. Port housing 18 includes as its primary components: a main inlet port 20 fluidically coupled to a main fluid flow channel 21 (shown in FIG. 2), which may be optionally equipped with a main port closure 22 attached by a, e.g., flexible arm or flange; fluid inlet port housings 24 (shown in FIG. 2 as 24A and 24B), each fluidically coupled to a fluid flow channel 34 (shown in FIG. 2 as 34A and 34B), and each optionally having their own closures 28, which may be attached by a, e.g., flexible arm or flange; one or more optional valves 26 (e.g., a one-way valve as shown in FIG. 2), disposed, e.g., within main inlet port 20 and/or fluid inlet port housing 24; and a fitting 30 for connection to shaft 12.

The main body of port housing 18 may be generally cylindrical in shape, and molded of medical grade silicone or other suitable plastic or material known in the art. Port housing 18 and shaft 12 may be connected via fitting 30 by silicone adhesive or other suitable material, or alternatively, port housing 18 and shaft 12 may be molded as a unitary structure.

In one embodiment, main inlet port 20 is a food inlet, as in the case of a gastrostomy tube assembly. Main inlet port 20 is fluidically coupled to main fluid flow channel 21 (shown in FIG. 2), which extends longitudinally through shaft 12, and is operable to channel food through the catheter 10 to a patient. Main inlet port 20 includes optional valve 26, which may be a conventional slit valve insert or membrane as known in the art. Valve 26 may also be molded of silicone or other suitable material. In one embodiment, valve 26 includes a slit that is forced open into a generally cylindrical shape by a feeding supply tube connector tip (not shown) when the tip is inserted in main inlet port 20 for feeding purposes. When the tip is removed, valve 26 is subjected to pressure from below, and the slit closes.

Main fluid flow channel 21 may be a cylindrical tube manufactured from medical grade silicone or other suitable material. In another embodiment, main fluid flow channel 21 is a void in or bore through shaft 12, which may be defined by a mold during manufacturing.

Each fluid inlet port housing 24 comprises a fluid inlet port 32 (shown in FIG. 2 as 32A and 32B) for receiving and channeling a fluid (e.g., ambient air, a gas, a liquid, saline, or other appropriate fluid) to a fluid flow channel 34 (shown in FIG. 2 as 34A and 34B). Each fluid inlet port housing 24 may include an optional valve (not shown), which may be a conventional slit valve insert, as known in the art. The optional valve may also be molded of silicone or other suitable material.

Each fluid inlet port 32 may receive a fluid via a fluid supply (not shown) such as an air pump, a syringe, or other suitable fluid supply, fluidly coupled (i.e., physically coupled directly or indirectly) to fluid inlet port 32.

In the embodiment illustrated in FIGS. 1 and 2, catheter 10 includes two fluid inlet port housings 24, designated as 24A and 24B. The two fluid inlet port housings 24 are each fluidically coupled to a fluid flow channel 34, which are disposed within and extending longitudinally through shaft 12. As shown in FIG. 2, fluid inlet port housing 24A is fluidically coupled to fluid flow channel 34A, and fluid inlet port housing 24B is fluidically coupled to fluid flow channel 34B. Fluid flow channels 34A and 34B may be disposed adjacent to or generally parallel to main fluid flow channel 21, and are typically (but not necessarily) narrower in diameter than main fluid flow channel 21. Fluid flow channels 34A and 34B may be made of medical grade silicone or other suitable material. In another embodiment, fluid flow channels 34A and 34B are voids in or bores through shaft 12, each of which may be defined by a mold during manufacturing.

Figure 3:
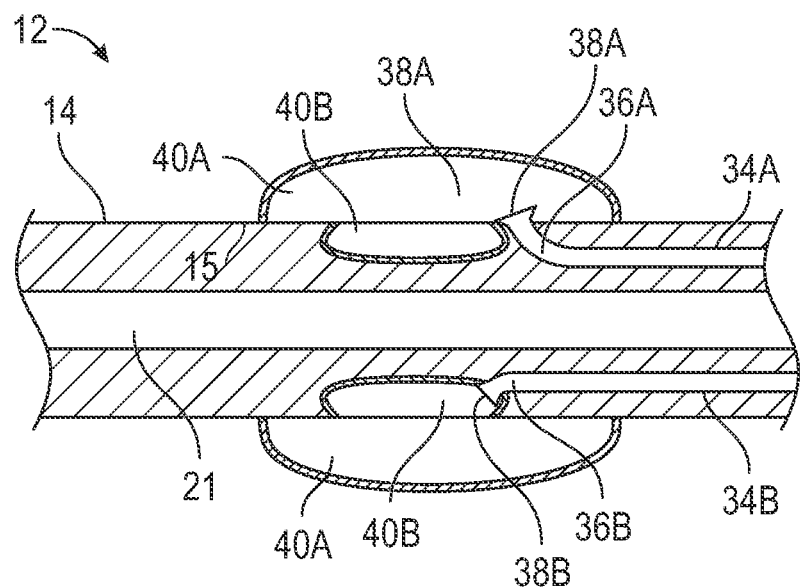
FIG. 3 is another cross-sectional view of a detail of the catheter of FIG. 1.

Fluid flow channels 34A and 34B terminate at balloon inflation ports 36, designated in FIG. 2 as 36A and 36B, respectively. Balloon inflation ports 36 fluidically couple fluid flow channels 34 and a balloon inflation orifice 38 (shown in FIGS. 3 and 4 as 38A and 38B). Balloon inflation orifices 38 are apertures or openings that permit the fluid channeled by fluid flow channels 34 to enter balloons 40. Balloon inflation ports 36 may further comprise an optional valve that is forced to open when subjected to fluid pressure, and close when the fluid pressure is removed.

As shown in the embodiments illustrated in FIGS. 1-5, selectively inflatable external balloon 40A is secured to and generally girdles the outer surface wall 14 of shaft 12, preferably by means of an adhesive bond such as a silicone adhesive. Balloon inflation port 36A extends from fluid flow channel 34A through outer surface wall 14 to balloon inflation orifice 38A. As such, the fluid flow channel 34A is capable of channeling fluid from fluid inlet 32A into selectively inflatable external balloon 40A so as to permit the expansion or inflation of the balloon.

Figure 4:
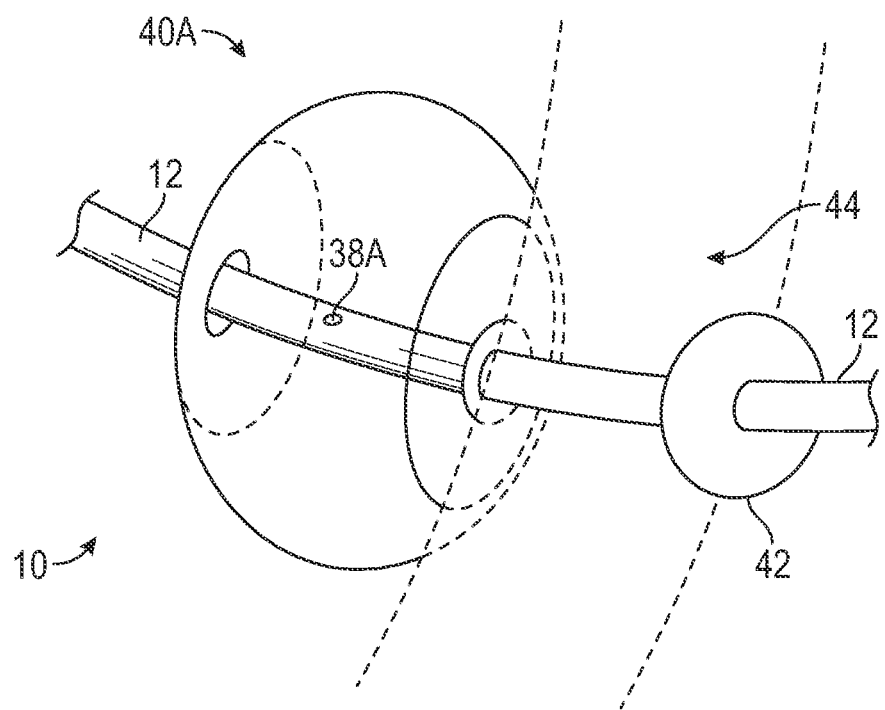
FIG. 4 illustrates an example of a catheter positioned through a stoma having a selectively inflatable external balloon operable as a bolster, wherein the selectively inflatable selectively inflatable external balloon is inflated and operating as a bolster.
Figure 5:
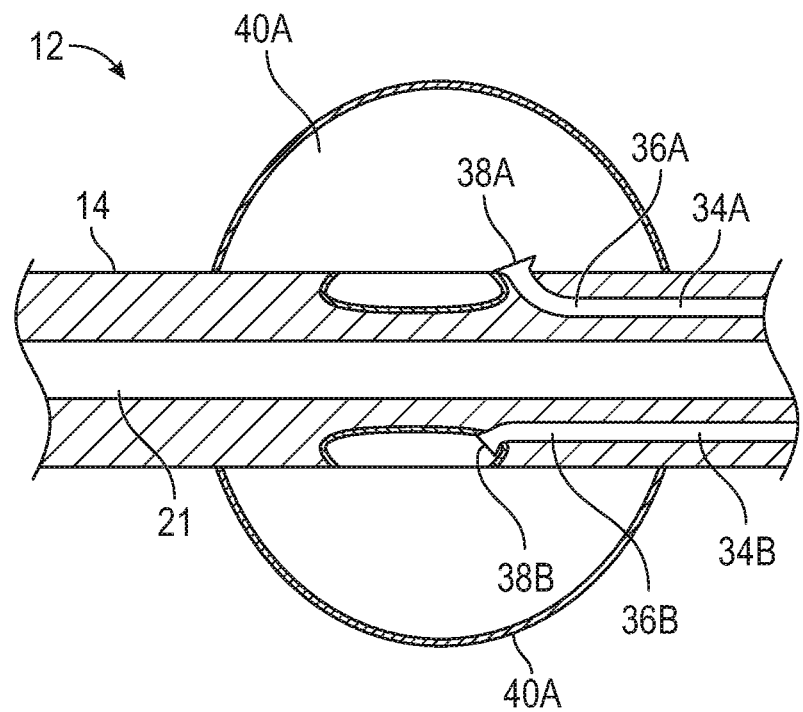
FIG. 5 illustrates a cross-sectional view of the catheter of FIG. 1 where the selectively inflatable external balloon is inflated.

For example, selectively inflatable external balloon 40A may be disposed on the outer surface wall 14 and around the circumference of shaft 12, enclosing balloon inflation orifice 38A. Fluid inlet 32A is, as a result, fluidically coupled to selectively inflatable external balloon 40A by fluid flow channel 34A. When a fluid is channeled or pumped in fluid inlet 32A and through fluid flow channel 34A, and then through balloon inflation port 36A and balloon inflation orifice 38A, the selectively inflatable external balloon 40A is inflated or expanded, e.g., as shown in FIGS. 4 and 5.

In one embodiment, the catheter may be a gastrointestinal feeding tube, and selectively inflatable external balloon 40A may be used as a bolster. In this embodiment, distal end 60 of shaft 12 as well as the then-unexpanded selectively inflatable external balloon 40A pass through a stoma in the human body 44 and ultimately through stomach lining as set forth in FIG. 4. Once the portion of shaft 12 surrounded by selectively inflatable external balloon 40A has entered the stomach, selectively inflatable external balloon 40A is expanded by supplying a fluid, e.g., saline via a syringe, to fluid inlet 32A, which channels the fluid to and through fluid flow channel 34A, which in turn channels the fluid to balloon inflation port 36A and on through balloon inflation orifice 38A and into selectively inflatable external balloon 40A, thereby causing selectively inflatable external balloon 40A to inflate or expand. Catheter 10 is then retracted through the stoma until selectively inflatable external balloon 40A comes into contact with the stomach lining. External balloon 40A thereby forms a seal for the stoma and prevents catheter 10 from moving further out of the stoma. Catheter 10 may further optionally include a retention device 42 (e.g., a silicone bumper) to help stabilize or position the catheter in relation to a stoma on a human body, or prevent the catheter from moving further into the body.

Turning back to FIGS. 2 and 3, fluid flow channel 34B terminates at balloon inflation port 36B. Balloon inflation port 36B fluidically couples fluid flow channel 34B and a balloon inflation orifice 38B (shown in FIGS. 2 and 3). Like balloon inflation orifice 38A, balloon inflation orifice 38B is an aperture or opening that permits the fluid channeled by fluid flow channel 34B to enter internal balloon valve 40B. Balloon inflation port 36B may further comprise an optional valve that is forced to open when subjected to fluid pressure, and close when the fluid pressure is removed.

Internal balloon valve 40B girdles the surface of main fluid flow channel 21, referred to herein as a flow channel wall. Internal balloon valve 40B may be secured to an inner surface wall 15 of shaft 12, or, alternatively, the outer surface of main fluid flow channel 21, preferably by means of an adhesive bond such as a silicone adhesive. Balloon inflation port 36B extends from fluid flow channel 34B to balloon inflation orifice 38B on internal balloon valve 40B. As such, the fluid flow channel 34B is capable of passing fluid from fluid inlet 32B into internal balloon valve 40B so as to permit the inflation or expansion of the balloon.

Figure 6:
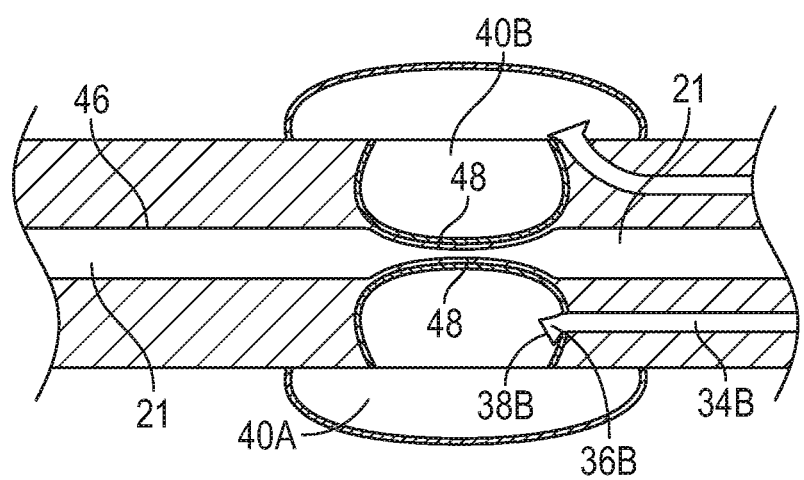
FIG. 6 is a cross-sectional view of an alternative embodiment of a catheter having a selectively inflatable external balloon and an internal balloon valve where the internal balloon valve is partially inflated.
Figure 7:
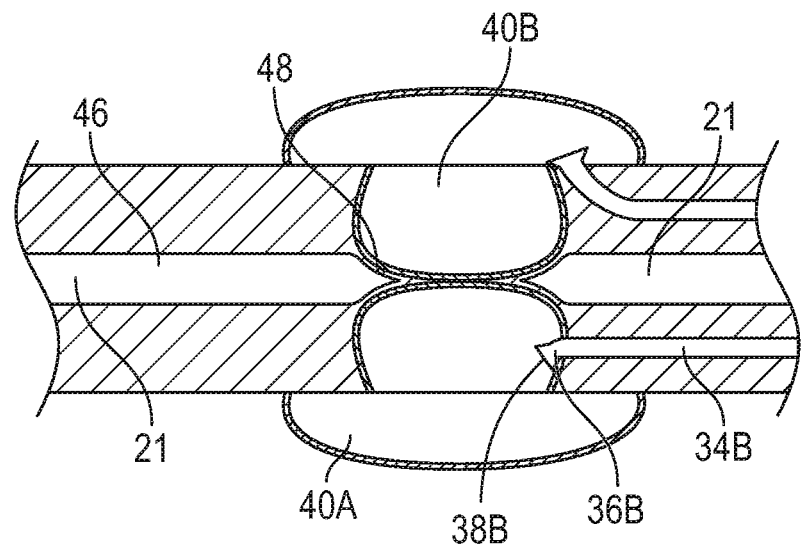
FIG. 7 is a cross-sectional view of the catheter of FIG. 6 where the internal balloon valve is substantially fully inflated.
Figure 9:
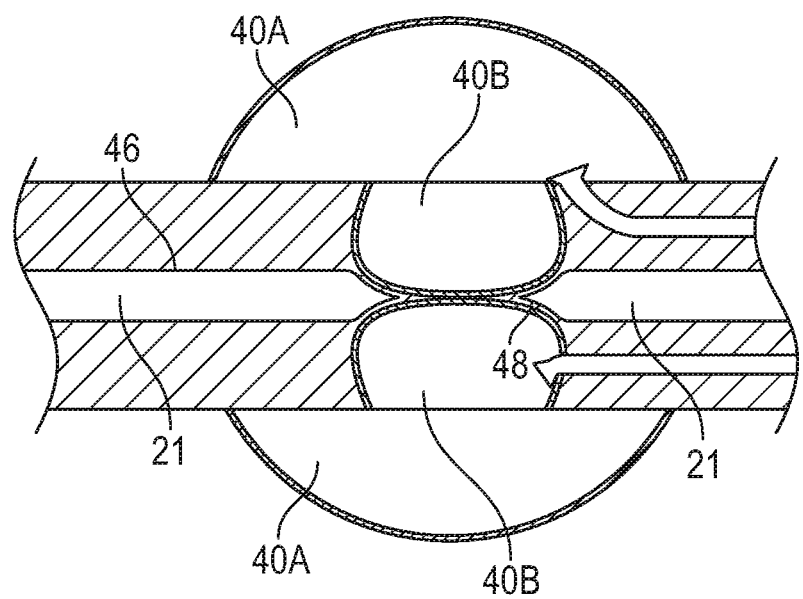
FIG. 9 is a cross-sectional view of the catheter of FIG. 8, wherein both the selectively inflatable external balloon and internal balloon valve are fully inflated.

For example, internal balloon valve 40B may be attached to an inner surface wall 15 of shaft 12 using silicone adhesive, enclosing balloon inflation orifice 38B and encircling main fluid flow channel 21, such that fluid inlet 32B is fluidically coupled to internal balloon valve 40B by fluid flow channel 34B. When a fluid is channeled or pumped into fluid inlet 32B and through fluid flow channel 34B, and then through balloon inflation port 36B and balloon inflation orifice 38B, the internal balloon valve 40B is inflated or expanded, as shown in FIGS. 6 and 7. And, as shown in FIG. 9, both balloons 40A and 40B may be inflated simultaneously.

Main fluid flow channel 21 is defined by flow channel wall 46, which may include thinner or more malleable portions in proximity to internal balloon valve(s) 40 designated as flow channel wall 48. When internal balloon valve 40B is inflated or expanded, it exerts a force upon flow channel wall 48 such that flow channel wall 48 compresses, bows, bends, or otherwise distends inwardly, ultimately collapsing or closing main fluid flow channel 21, as shown in FIG. 6. Internal balloon 40B thus acts as a flexible valve to restrict and ultimately selectively stop the free flow of fluids through main fluid flow channel 21.

In one embodiment, the thickness of flow channel wall 46 may vary along the length of main fluid flow channel 21. In one example, the portion of flow channel wall 46 in proximity to or in contact with internal balloon valve 40B (i.e., flow channel wall 48) is less thick, or is relativity thinner, than the remainder of flow channel wall 46, as shown in FIG. 7. In this example, that portion of flow channel wall 48 is sufficiently thin that the inflation or expansion of internal balloon valve 40B bows flow channel wall 48 around its entire circumference, or 360 degrees around main fluid flow channel 21. Increasing the amount of inflation or expansion of internal balloon valve 40B will in turn increase the bowing or compression of flow channel wall 48 until main fluid flow channel 21 is impassable or substantially closed.

Figure 8:
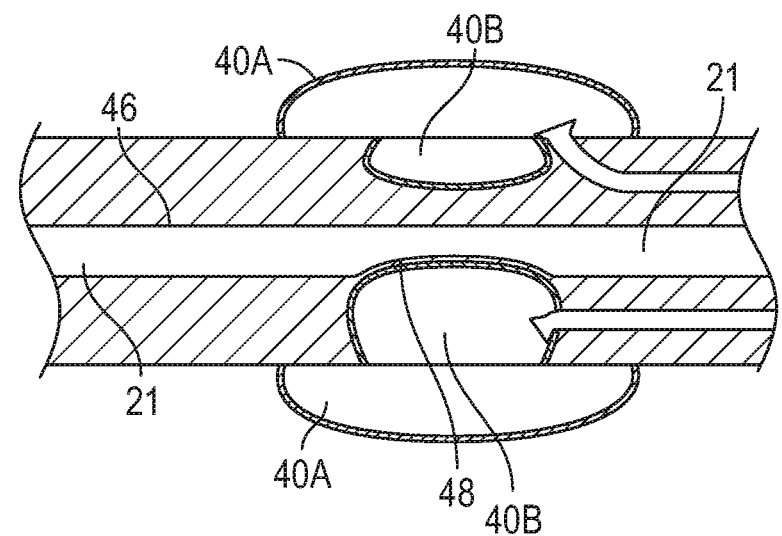
FIG. 8 is a cross-sectional view of another example of a catheter having a selectively inflatable external balloon and an internal balloon valve where the internal balloon valve is partially inflated and exerting a compression force or pressure on the shaft.
Figure 13:
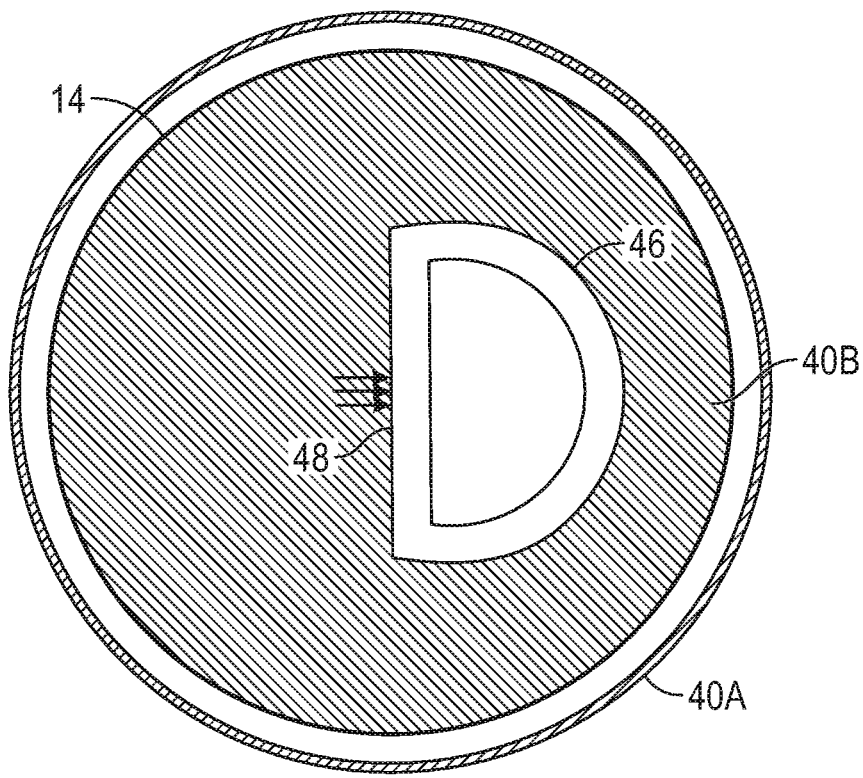
FIG. 13 is an end-on, cross-sectional view of alternative embodiment of a catheter having a selectively inflatable external balloon and an internal balloon valve.

In an alternative embodiment illustrated in FIGS. 8 and 13, only a portion of flow channel wall 48 is sufficiently thin that the inflation or expansion of internal balloon valve 40B bows that portion of flow channel wall 48. As a result, the inflation or expansion of internal balloon valve 40B will only bow flow channel wall 48 around a portion of its circumference, e.g., 180 degrees around main fluid flow channel 21. The remainder of flow channel wall 46 is thick enough (or composed of sufficiently strong material) to withstand the pressure from the inflating or expanding internal balloon valve 40B. As a result, internal balloon valve 40B restricts only a portion of the free flow of fluids through main fluid flow channel 21.

Figure 10:
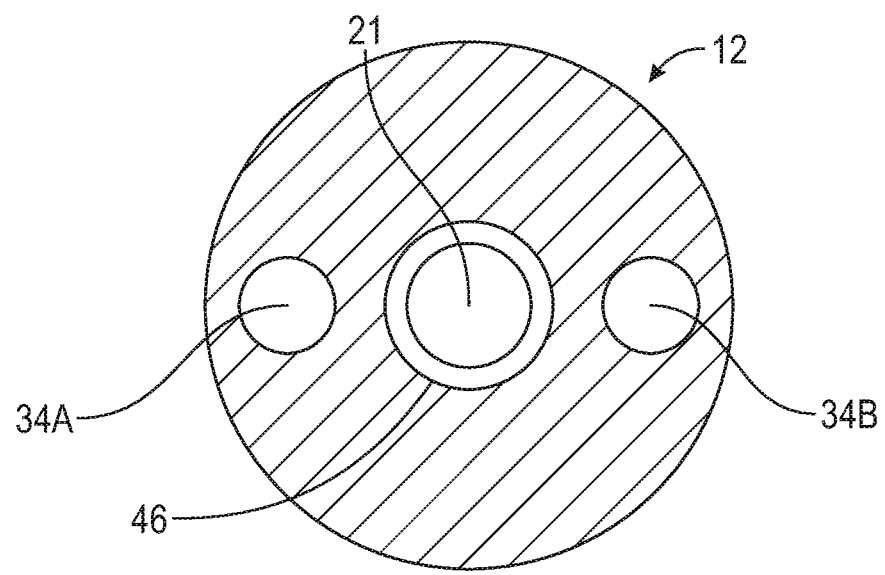
FIG. 10 is an end-on, cross-sectional view of the embodiment of a catheter having a the selectively inflatable external balloon and an internal balloon valve shown in FIG. 2 at "A".
Figure 11:
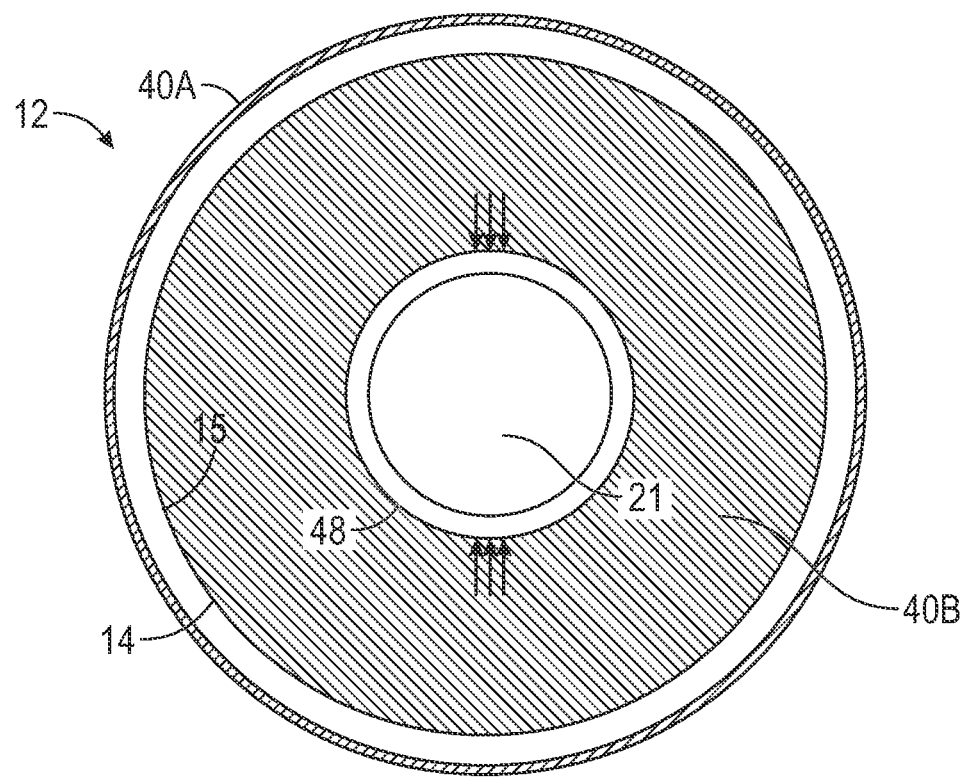
FIG. 11 is an end-on, cross-sectional view of the embodiment of a catheter having a selectively inflatable external balloon and an internal balloon valve shown in FIG. 2 at "B".
Figure 12:
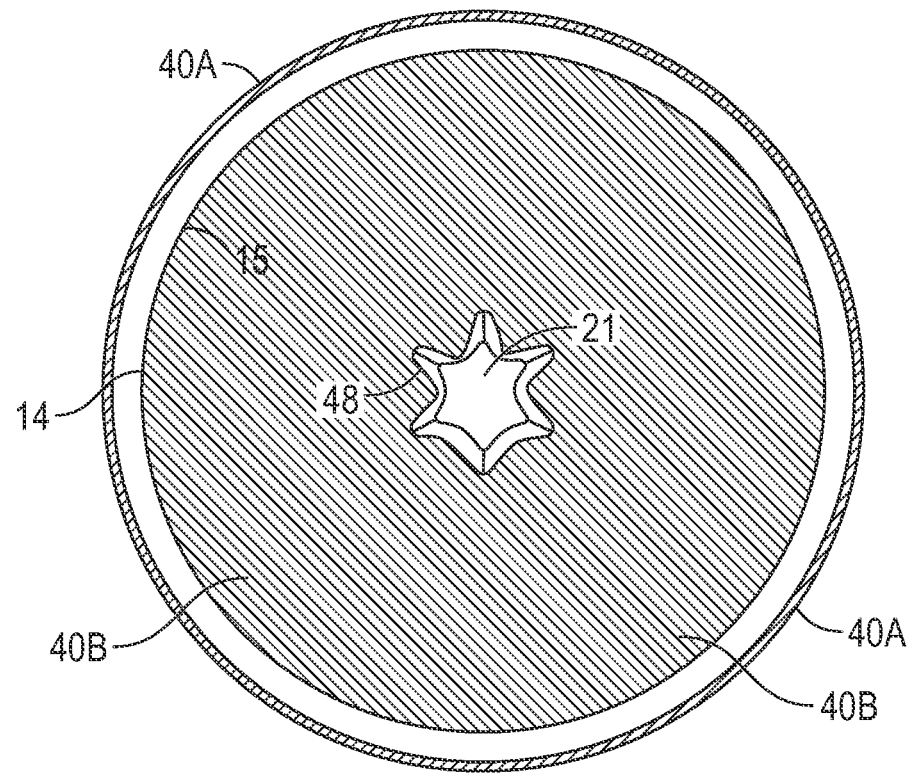
FIG. 12 is an end-on, cross-sectional view of another embodiment of the catheter having a selectively inflatable external balloon and an internal balloon valve shown in FIG. 11.

Exemplary cross-sections of the effect of an internal balloon valve are illustrated in FIGS. 10, 11, 12, and 13. FIGS. 10 and 11 are cross-sections "A" and "B" of the catheter 10 illustrated in FIGS. 1 and 2. More particularly, FIG. 10 depicts the cross-section "A" located "upstream" from the balloons 40. FIG. 11 depicts the cross-section "B" at the position of the balloons 40. In this cross-section B, flow channel wall 48 is thinner than the up-stream flow channel wall 46 shown in FIG. 10 such that the pressure from internal balloon valve 40B, when expanded or inflated around main fluid flow channel 21 causes flow channel wall 48 to collapse inward until main fluid flow channel 21 is substantially closed, as shown in FIG. 12.

Alternatively, as shown in FIG. 13, only a portion of flow channel wall 48 is thinner than the flow channel wall 46, such that the pressure from inflated internal balloon valve 40B around main fluid flow channel 21 causes the thinner portion of flow channel wall 48 to collapse inward until main fluid flow channel 21 is restricted about 180 degrees around its circumference. Thicker (or otherwise stronger or more resilient) flow channel wall 46 resists the compression force or pressure (illustrated by arrows) exerted by inflating internal balloon valve 40B.

The circumference of main fluid flow channel 21 may be, for example, sized from about 5 French to less than 24 French, and the longitudinal length of a flow channel wall 48 near to or in contact with internal balloon valve 40B may be selected from 5 millimeters to 30 millimeters, depending on the volume of the internal balloon valve. The thickness of flow channel wall 46 may be 0.25 mm to 1.25 mm, depending on the circumference of main fluid flow channel 21, and the thickness of flow channel wall 48 may be 0.25 mm to 1.25 mm, depending on the circumference of main fluid flow channel 21 and the volume of the internal balloon valve.

As will be evident to one of ordinary skill in the art, the relative thickness of the flow channel wall of main fluid flow channel 21 will depend upon the materials selected for, and the amount of pressure potentially exerted by, internal balloon valve 40B, and the structural soundness required to perform main fluid flow channel 21's function (e.g., channeling food, etc.) over a long period of time.

In yet another embodiment, the catheter may be a gastrointestinal feeding tube, and selectively inflatable external balloon 40A may be used as a bolster. In this embodiment, distal end 60 of shaft 12 as well as the then-unexpanded selectively inflatable external balloon 40A pass through a stoma in the human body 44, including a plurality of tissue layers and ultimately through stomach lining as set forth in FIG. 4. Once the portion of shaft 12 surrounded by selectively inflatable external balloon 40A has entered the stomach, selectively inflatable external balloon 40A is expanded by supplying a fluid, e.g., saline via a syringe. At the same time, before, or thereafter, internal balloon valve 40B is expanded by supplying a fluid, e.g., ambient air via a syringe, which in turn compresses flow channel wall 48 of main fluid flow channel 21, such that air, fluid or other contents in the stomach are prevented from flowing back through main fluid flow channel 21 past internal balloon valve 40B. The compression force exerted by internal balloon valve 40B on flow channel wall 48 of main fluid flow channel 21 may be selectively increased or decreased across a gradient for desired effect. For example, the compression force or pressure selected may be such that pastes or liquids inserted at main inlet port 20, under pressure (e.g., by a syringe or feeding pump), proceed through main fluid flow channel 21 past internal balloon valve 40B. Alternatively, pastes or liquids inserted at main inlet port 20, under pressure (e.g., by a syringe or feeding pump), may proceed through main fluid flow channel 21 and not pass internal balloon valve 40B, which remains substantially closed. In another example, pastes or liquids may be inserted at main inlet port 20 under pressure and proceed through main fluid flow channel 21 past internal balloon valve 40B, but the flow may be restricted by internal balloon valve 40B.

The expansion or inflation of selectively inflatable external balloon 40A does not interfere with the expansion or inflation of internal balloon valve 40B, and as shown, both selectively inflatable external balloon 40A and internal balloon valve 40B may be selectively inflated or expanded at the same or different times.

In another example, an instrument, e.g., a blunt tip catheter with side holes near the blunt tip, may be physically pushed or guided through main fluid flow channel 21 and past internal balloon valve 40B when the pressure applied to move the instrument is greater than the pressure exerted by internal balloon valve 40B on flow channel wall 48 that is keeping main fluid flow channel 21 closed. Such an instrument may be used to feed or drain fluid or air from a cavity, while internal balloon valve 40B performs a seal or valve function to prevent fluid or air from leaking around the instrument, e.g., during feeding or drainage.

In a further example, internal balloon valve 40B may be disposed within shaft 12 away from selectively inflatable external balloon 40A, e.g., nearer to the distal end 60 of shaft 12. Alternatively, or in addition to this embodiment, internal balloon valve 40B is disposed nearer to the proximal end of shaft 12.

Figure 14:
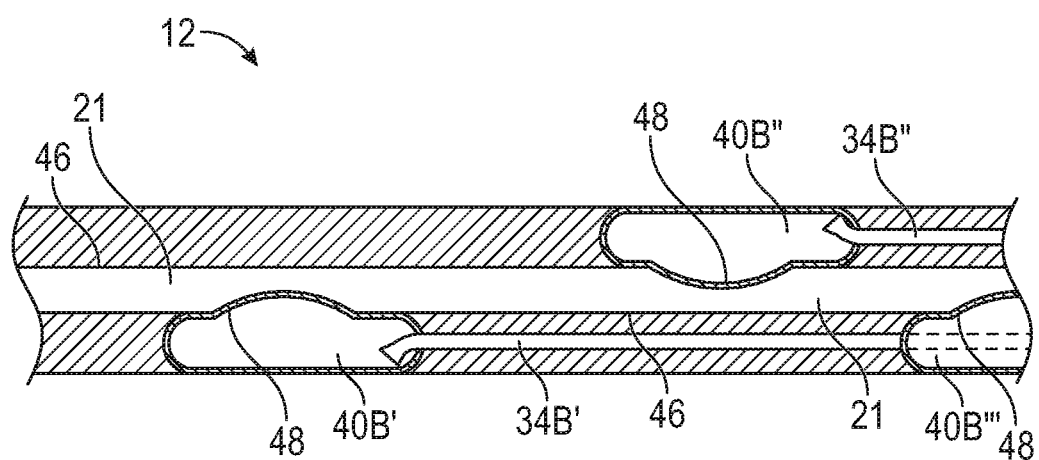
FIG. 14 is a cross-sectional view of alternative embodiment of a catheter having a plurality of internal balloon valves.

In another embodiment, there may be several internal balloon valves 40 disposed along a longitudinal length of shaft 12, each fluidly connected to the same or different fluid flow channels 34 such that each may be inflatable or expandable independently or together, as depicted in FIG. 14. FIG. 14 illustrates a plurality of internal balloon valves 40B', 40B", and 40B'" disposed in alternating positions along the longitudinal axis of main fluid flow channel 21 and in fluid connection with different fluid flow channels 34 (e.g., 34B', 34B", and 34B'"). When all inflated, internal balloon valves 40B', 40B", and 40B'" may be used to restrict the flow of fluid through main fluid flow channel 21.

In an alternative embodiment, internal balloon valve 40B may run substantially the length of an inner surface wall 15 of shaft 12, or have any suitable longitudinal length.

Figure 15:
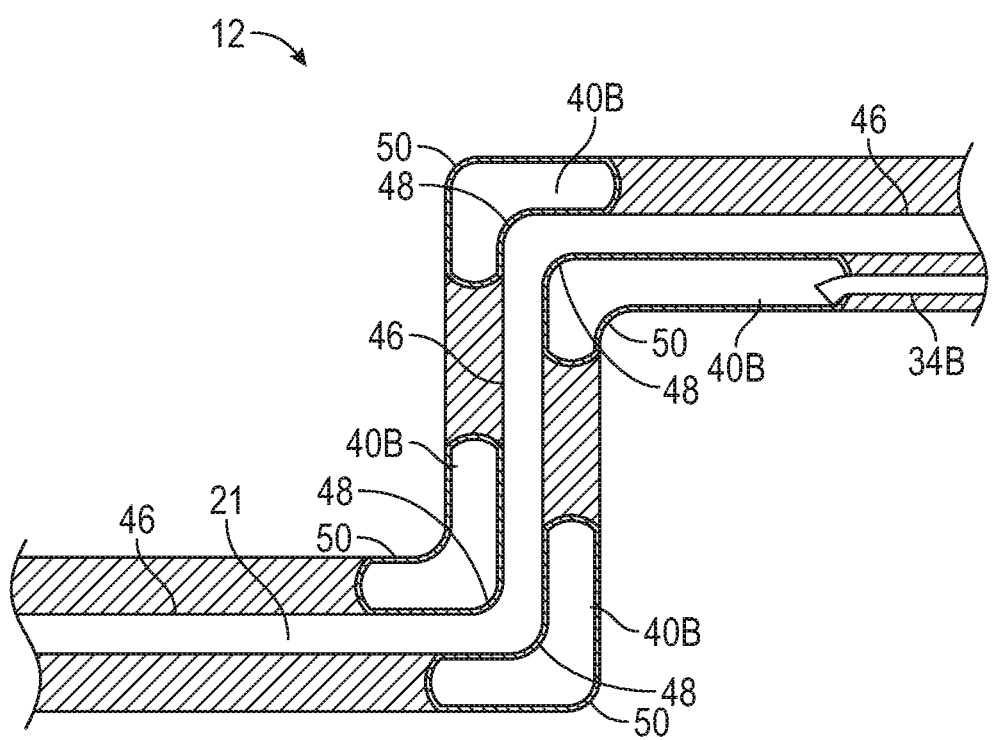
FIG. 15 is a cross-sectional view of alternative embodiment of a catheter having a plurality of internal balloon valves that when inflated cause kinks in the shaft of the catheter.

Turning to FIG. 15, another embodiment of catheter 10 is shown, where outer surface wall 14 of shaft 12 may be, for example, selectively thinned such that the pressure from internal balloon valve 40B, when expanded or inflated, exerts a pressure on a portion of flow channel wall 48 of main fluid flow channel 21 and thin outer surface portion 50, causing outer surface wall 14 to kink, thereby slowing or restricting the rate of flow of a fluid through main fluid flow channel 21. Such a restriction may be particularly useful at or near the distal end 60 of shaft 12 near, e.g., outlet port 62, which may have an aperture or opening for releasing content like food from main fluid flow channel 21 and be subject to back-flow or reflux from a stomach or other cavity. Fluid channeled through main fluid flow channel 21 under pressure (e.g., by a pump or from a syringe) will be able to transverse the kink, but back-flow from a cavity will not travel past the kink in the other direction. Distal end 60 of shaft 12 may have additionally have an end portion that may be beveled or tapered. Outlet port 62 may itself have a circular cross-section or other appropriate shape. Alternatively, in a further embodiment, shaft 12 (rather than having selectively thinned walls) may be constructed with certain structural features, such as wire or other structures known to those of skill in the art referred to herein as kinking structures, such that the pressure from internal balloon valve 40B, when expanded or inflated, exerts a pressure on a portion of shaft 12, causing the kinking structure to activate and kink shaft 12, thereby slowing or restricting the rate of flow of a fluid through main fluid flow channel 21.

Figure 16:
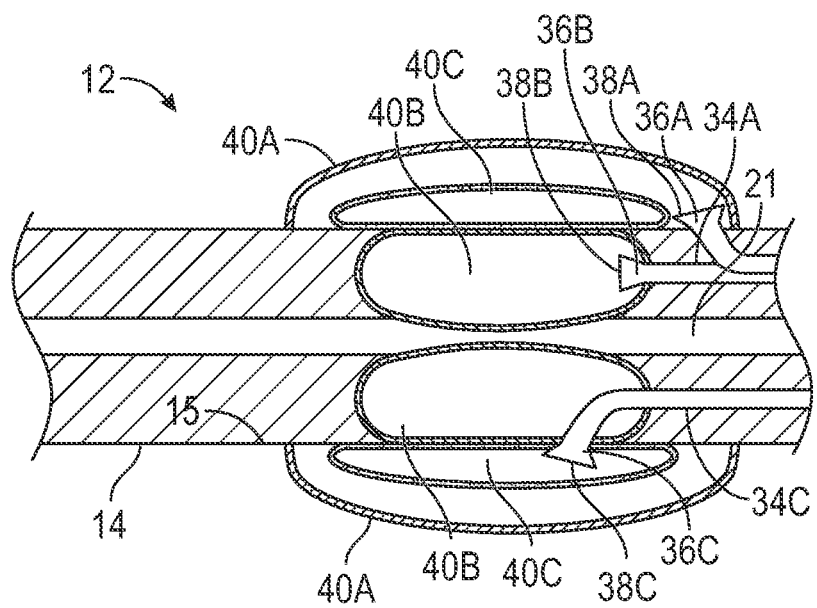
FIG. 16 is a cross-sectional view of alternative embodiment of a catheter having a selectively inflatable external balloon and an internal balloon valve, and a further middle balloon disposed within the selectively inflatable external balloon.
Figure 17:
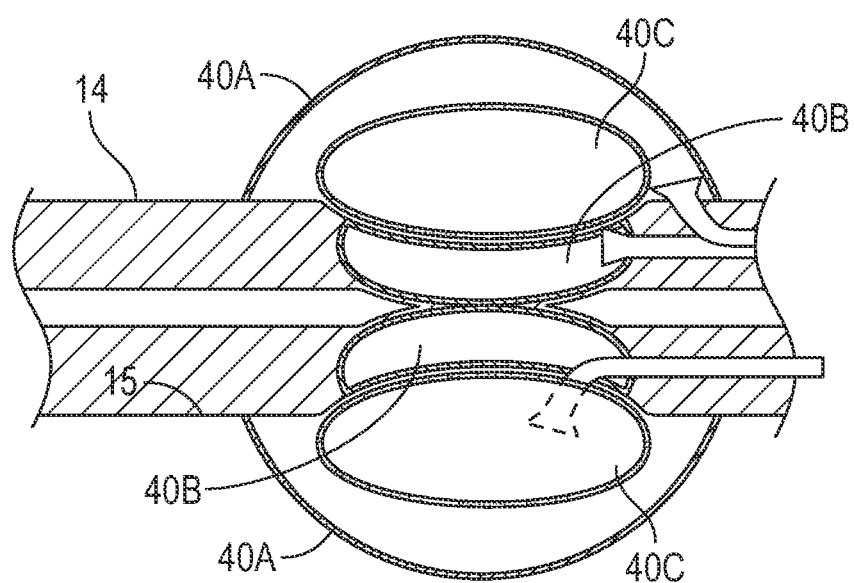
FIG. 17 is a cross-sectional view of the catheter of FIG. 16 where the selectively inflatable external balloon and middle balloon are inflated.

Turning to FIGS. 16 and 17, a further embodiment of a catheter is shown having a plurality of concentric balloons. In particular, the device of FIG. 16 is shown including a selectively inflatable external balloon 40A and internal balloon valve 40B, and a further middle balloon 40C disposed within selectively inflatable external balloon 40A. Like in the foregoing embodiments, selectively inflatable external balloon 40A (or middle balloon 40C, or both) may be used as a bolster. External balloon 40A, internal balloon valve 40B, and/or middle balloon 40C are selectively expanded by supplying a fluid, e.g., saline via a syringe, through fluid flow channels 34A (fluidically connected to selectively inflatable external balloon 40A), 30B (fluidically connected to internal balloon valve 40B), and 34C (fluidically connected to middle balloon 40C), which are disposed within and extending longitudinally through shaft 12. In an alternative embodiment, internal balloon valve 40B is not fluidically connected to a fluid flow channel. Fluid flow channels 34A, 34B, and 34C may be made of medical grade silicone or other suitable material and terminate at balloon inflation ports 36A, 36B and 36C, respectively, which fluidically couple the fluid flow channels 34A, 34B and 34C and the balloons (e.g., through an inflation orifice, as discussed above). External balloon 40A is secured to and generally girdles the outer surface wall 14 of shaft 12, preferably by means of an adhesive bond such as a silicone adhesive. Middle balloon 40C is disposed within or surrounded by selectively inflatable external balloon 40A. Middle balloon 40C is expanded by supplying a fluid, e.g., ambient air via a syringe, which in turn compresses a portion of flow channel wall 48 of main fluid flow channel 21 and/or internal balloon valve 40B, such that air, fluid or other contents in the stomach are prevented from flowing back through main fluid flow channel past internal balloon valve 40B. The compression force exerted by middle balloon 40C on the flow channel wall and/or internal balloon valve 40B may be selectively increased or decreased across a gradient for desired effect, like in the embodiments discussed above. The expansion or inflation of selectively inflatable external balloon 40A does not interfere with the expansion or inflation of middle balloon 40C (except to the extent that middle balloon 40C can only be expanded so far as the capacity of selectively inflatable external balloon 40A will permit; the capacity determinations are well within the skill of the ordinary artisan to select). And as shown in FIG. 17, both selectively inflatable external balloon 40A and middle balloon 40C may be selectively inflated or expanded at the same or different times. Additionally, should selectively inflatable external balloon 40A collapse or otherwise fail, middle balloon 40C may assume the function as a bolster, if needed.

Figure 18:
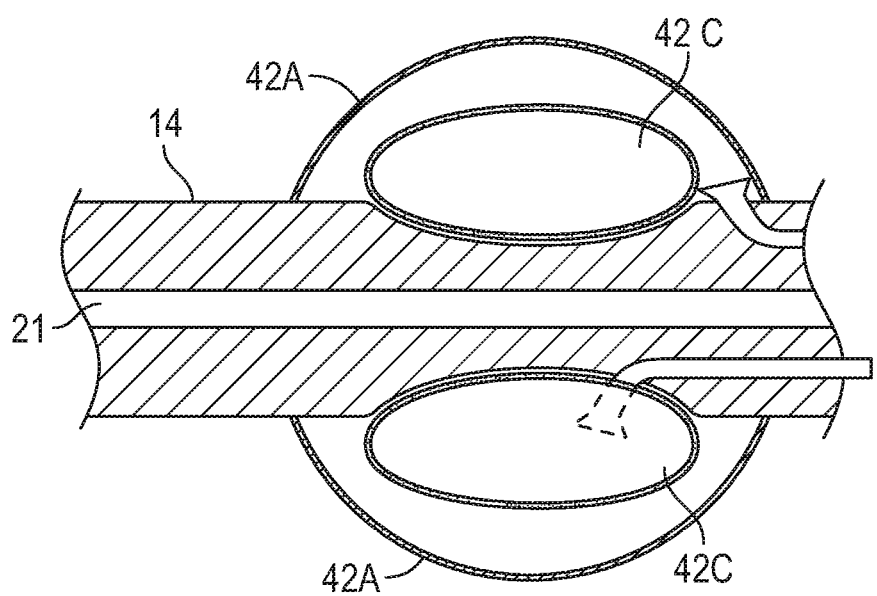
FIG. 18 is a cross-sectional view a further embodiment of a catheter having a selectively inflatable external balloon and a middle balloon disposed within the selectively inflatable external balloon.

Turning to FIG. 18, a further embodiment of a catheter is shown having a plurality of concentric balloons disposed outside of the shaft wall instead of between the shaft wall and the main flow channel. In these embodiments, both the shaft wall and the main flow channel wall may be thinned in the section engirdled by the concentric balloons to allow the balloons to compress the shaft wall and main flow channel when distended. In particular, the device of FIG. 18 is shown including a selectively inflatable external balloon 42A and a middle balloon 42C disposed within selectively inflatable external balloon 42A. Like in the foregoing embodiments, selectively inflatable external balloon 42A (or middle balloon 42C, or both) may be used as a bolster. External balloon 42A and/or middle balloon 42C are selectively expanded by supplying a fluid, e.g., saline via a syringe, through fluid flow channels fluidically connected to selectively inflatable external balloon 42A and 42C, which are disposed within and extending longitudinally through shaft 12. Like in other embodiments, fluid flow channels may be made of medical grade silicone or other suitable material and terminate at balloon inflation ports, which fluidically couple the fluid flow channels and the balloons (e.g., through an inflation orifice, as discussed above). External balloon 42A is secured to and generally girdles the outer surface wall 14 of shaft 12, preferably by means of an adhesive bond such as a silicone adhesive. Middle balloon 42C is disposed within or surrounded by selectively inflatable external balloon 42A. Middle balloon 42C is expanded by supplying a fluid, e.g., ambient air via a syringe, which in turn compresses a portion of flow channel wall 48 of main fluid flow channel 21, such that air, fluid or other contents in the stomach are prevented from flowing back through main fluid flow channel. The compression force exerted by middle balloon 42C on the flow channel wall may be selectively increased or decreased across a gradient for desired effect, like in the embodiments discussed above. The expansion or inflation of selectively inflatable external balloon 42A does not interfere with the expansion or inflation of middle balloon 42C (except to the extent that middle balloon 42C can only be expanded so far as the capacity of selectively inflatable external balloon 42A will permit; the capacity determinations are well within the skill of the ordinary artisan to select). Both selectively inflatable external balloon 42A and middle balloon 42C may be selectively inflated or expanded at the same or different times. Additionally, should selectively inflatable external balloon 42A collapse or otherwise fail, middle balloon 42C may assume the function as a bolster, if needed.

It will be readily apparent to one of ordinary skill in the art that the catheter having a balloon valve may be useful in several medical procedures, including gastrostomy assemblies, pulmonary drainage assemblies, colostomy assemblies, bladder drainage assemblies, gas release assemblies, fluid collection assemblies, vascular assemblies (including carotid stents) and others where temporarily controlling fluid flow through a catheter is desirable.

This detailed description provides examples including features and elements of the claims for the purpose of enabling a person having ordinary skill in the art to make and use the inventions recited in the claims. However, these examples are not intended to limit the scope of the claims, directly. Instead, the examples provide features and elements of the claims that, having been disclosed in these descriptions, claims and drawings, may be altered and combined in ways that are known in the art.

What is claimed is:

1. A catheter comprising:
   a proximal end and a distal end opposite the proximal end;
   a port housing disposed near the proximal end having a main inlet port fluidically-coupled to a main fluid flow channel having a flow channel wall with an outer surface, and two or more fluid inlet port housings each fluidically coupled to an associated fluid flow channel;
   a cylindrical shaft having an outer surface wall and an inner surface wall enclosing the fluid flow channels;
   a fitting connecting the port housing to the cylindrical shaft;
   wherein the main fluid flow channel extends longitudinally through the cylindrical shaft from the proximal end to the distal end of the catheter;
   wherein the two or more fluid inlet port housings each further comprise an associated fluid inlet port for receiving and channeling a fluid;
   wherein each of the associated fluid flow channels are disposed within and extend longitudinally through the cylindrical shaft, and each of the associated fluid flow channels terminate at an associated balloon inflation port that is fluidically coupled to an associated balloon inflation orifice operable to channel fluid into a balloon;
   a selectively inflatable external balloon secured to and engirdling a portion of the outer surface wall of the cylindrical shaft and enclosing one of the balloon inflation orifices, wherein the selectively inflatable external balloon is thereby fluidically coupled to the balloon inflation port, fluid flow channel, and fluid inlet port associated with that balloon inflation orifice;
   an internal balloon valve disposed between the inner surface wall of the cylindrical shaft and the outer surface of the flow channel wall of the main fluid flow channel, wherein the internal balloon valve is secured to and engirdles a portion of the flow channel wall of the main fluid flow channel by surrounding the main fluid flow channel circumferentially and encloses one of the balloon inflation orifices, whereby the internal balloon valve is fluidically coupled to the balloon inflation port, fluid flow channel, and fluid inlet port associated with that balloon inflation orifice, and wherein the balloon inflation orifice enclosed by the internal balloon valve is different from the balloon inflation orifice enclosed by the selectively inflatable external balloon;
   wherein the internal balloon valve, when fully inflated, distends a portion of the flow channel wall inwardly such that the main fluid flow channel is closed and impassable except for fluids introduced to the main inlet port under pressure; and
an outlet port disposed at the distal end fluidically coupled to the main fluid flow channel.

2. The catheter of claim 1, wherein the cylindrical shaft has circumference of between about 5 French to 24 French.

3. The catheter of claim 1, wherein the cylindrical shaft is between about 2 cm to about 37 cm in length.

4. The catheter of claim 1, wherein the catheter is a gastrostomy tube assembly.

5. The catheter of claim 1, wherein the main fluid flow channel is a bore through the cylindrical shaft defined by a mold during fabrication.

6. The catheter of claim 1, wherein the flow channel wall able to be contacted by the internal balloon valve is less thick than the flow channel wall not able to be contacted by the internal balloon valve.

7. The catheter of claim 1, wherein force exerted by the internal balloon valve on the flow channel wall of the main fluid flow channel is selectively adjustable to increase or decrease an amount of fluid flowing through the main fluid flow channel.

8. The catheter of claim 1, further comprising a blunt tip catheter guidable through the main fluid flow channel and past the internal balloon valve when inflated.

9. The catheter of claim 1, further comprising two or more internal balloon valves disposed along a longitudinal length of the main fluid flow channel, wherein each of the two or more internal balloon valves is fluidically coupled to a different fluid flow channel.

10. The catheter of claim 1, further comprising two or more internal balloon valves disposed in alternating positions along a longitudinal axis of the main fluid flow channel.

11. The catheter of claim 1, wherein a portion of the outer surface wall of the cylindrical shaft is thinned such that a force exerted by the internal balloon valve when inflated causes the outer surface wall to kink, thereby restricting fluid flow through the main fluid flow channel.

12. A catheter comprising:
a proximal end and a distal end opposite the proximal end;
a port housing disposed near the proximal end having a main inlet port fluidically coupled to a main fluid flow channel having a flow channel wall, and two or more fluid inlet port housings each fluidically coupled to an associated fluid flow channel;
a cylindrical shaft having an outer surface wall enclosing the fluid flow channels;
a fitting connecting the port housing to the cylindrical shaft;
wherein the main fluid flow channel extends longitudinally through the cylindrical shaft from the proximal end to the distal end of the catheter;
wherein the two or more fluid inlet port housings each further comprise an associated fluid inlet port for receiving and channeling a fluid;
wherein each of the associated fluid flow channels are disposed within and extend longitudinally through the cylindrical shaft, and terminate at an associated balloon inflation port fluidically coupled to an associated balloon inflation orifice, which are each operable to channel fluid into a different balloon;
a selectively inflatable external balloon secured to and engirdling a portion of the outer surface wall of the cylindrical shaft and enclosing one of the balloon inflation orifices, whereby the selectively inflatable external balloon is fluidically coupled to the balloon inflation port, fluid flow channel, and fluid inlet port associated with that balloon inflation orifice;
a selectively inflatable middle balloon disposed within a cavity of the selectively inflatable external balloon and secured to and engirdling a portion of the outer surface wall of the cylindrical shaft and enclosing one of the balloon inflation orifices, wherein the selectively inflatable middle balloon is thereby fluidically coupled to the balloon inflation port, fluid flow channel, and fluid inlet port associated with that balloon inflation orifice;
wherein the balloon inflation orifice enclosed by the selectively inflatable external balloon is different from the balloon inflation orifice enclosed by the selectively inflatable middle balloon;
wherein the selectively inflatable middle balloon, when inflated, exerts pressure on the outer surface wall of the cylindrical shaft and the flow channel wall of the main fluid flow channel to restrict fluid flow through the main fluid flow channel except for fluids introduced to main inlet port under pressure; and
an outlet port disposed at the distal end fluidically coupled to the main fluid flow channel.

13. A catheter comprising:
a proximal end and a distal end opposite the proximal end;
a port housing disposed near the proximal end having a main inlet port fluidically coupled to a main fluid flow channel having a flow channel wall, and three or more fluid inlet ports each for receiving and channeling a fluid to an associated fluid flow channel;
a cylindrical shaft having an outer surface wall and an inner surface wall enclosing three or more fluid flow channels;
a fitting connecting the port housing to the cylindrical shaft;
wherein the main fluid flow channel extends longitudinally through the cylindrical shaft from the proximal end to the distal end of the catheter;
wherein each of the associated fluid flow channels are disposed within and extend longitudinally through the cylindrical shaft, and terminate at a separate balloon inflation port fluidically coupled to an associated balloon inflation orifice that is operable to channel fluid into a balloon;
a selectively inflatable external balloon secured to and engirdling a portion of the outer surface wall of the cylindrical shaft and enclosing one of the balloon inflation orifices, whereby the selectively inflatable external balloon is fluidically coupled to the balloon inflation port, fluid flow channel, and fluid inlet port associated with that balloon inflation orifice;
a selectively inflatable middle balloon disposed within a cavity of the selectively inflatable external balloon, and secured to and engirdling a portion of the outer surface wall of the cylindrical shaft by surrounding the portion of the outer surface wall of the cylindrical shaft circumferentially, and enclosing one of the balloon inflation orifices, whereby the selectively inflatable middle balloon is fluidically coupled to the balloon inflation port, fluid flow channel, and fluid inlet port associated with that balloon inflation orifice;
wherein the balloon inflation orifice enclosed by the selectively inflatable external balloon is different from the balloon inflation orifice enclosed by the selectively inflatable middle balloon;
wherein the selectively inflatable middle balloon, when inflated, exerts pressure on the outer surface wall of the cylindrical shaft and the flow channel wall of the main fluid flow channel to restrict fluid flow through the main fluid flow channel except for fluids introduced to main inlet port under pressure;

an internal balloon valve disposed inside the cylindrical shaft between the inner surface wall of the cylindrical shaft and an outer surface of the flow channel wall of the main fluid flow channel, and engirdling a portion of the flow channel wall of the main fluid flow channel; and an outlet port disposed at the distal end fluidically coupled to the main fluid flow channel.

14. A method of operating a catheter having an internal balloon valve, comprising the steps of:

inflating a selectively inflatable external balloon secured to and engirdling a portion of an outer surface wall of a cylindrical shaft of a catheter by:
  introducing a fluid to a first fluid inlet port disposed within a first fluid inlet port housing located at a proximal end of the catheter,
  channeling the fluid from the first fluid inlet port through a first fluid flow channel disposed within and extending longitudinally through the cylindrical shaft of the catheter to fill the selectively inflatable external balloon, wherein the first fluid flow channel is fluidically coupled to a first balloon inflation port fluidically coupled to the selectively inflatable external balloon; and inflating an internal balloon valve disposed inside the cylindrical shaft of the catheter between an inner surface wall of the cylindrical shaft and an outer surface of a flow channel wall of a main fluid flow channel, wherein the internal balloon valve engirdles a portion of the flow channel wall of the main fluid flow channel by surrounding the portion the flow channel wall circumferentially, and the main fluid flow channel is disposed within and extends longitudinally through the cylindrical shaft of the catheter, by:
  introducing a second fluid to a second fluid inlet port disposed within a second fluid inlet port housing located at the proximal end of the catheter,
  channeling the second fluid from the second fluid inlet port through a second fluid flow channel disposed within and extending longitudinally through the cylindrical shaft of the catheter to fill the internal balloon valve, wherein the second fluid flow channel is fluidically coupled to a second balloon inflation port fluidically coupled to the internal balloon valve, and distending a surface of the main fluid flow channel until the main fluid flow channel is closed and impassable.

15. A method of operating a catheter having an internal balloon valve, comprising the steps of:

inflating a selectively inflatable external balloon secured to and engirdling a portion of an outer surface wall of a cylindrical shaft of a catheter by:
  introducing a fluid to a first fluid inlet port disposed within a first fluid inlet port housing located at a proximal end of the catheter,
  channeling the fluid from the first fluid inlet port through a first fluid flow channel disposed within and extending longitudinally through the cylindrical shaft of the catheter to fill the selectively inflatable external balloon, wherein the first fluid flow channel is fluidically coupled to a first balloon inflation port fluidically coupled to the selectively inflatable external balloon; and inflating an internal balloon valve disposed within a cavity of the selectively inflatable external balloon and secured to and engirdling a portion of the outer surface wall of the cylindrical shaft of the catheter by:
  introducing a second fluid to a second fluid inlet port disposed within a second fluid inlet port housing located at the proximal end of the catheter,
  channeling the second fluid from the second fluid inlet port through a second fluid flow channel disposed within and extending longitudinally through the cylindrical shaft of the catheter to fill the internal balloon valve, wherein the second fluid flow channel is fluidically coupled to a second balloon inflation port fluidically coupled to the internal balloon valve, and
  distending a surface of a main fluid flow channel of the catheter until the main fluid flow channel is closed and impassable.

* * * * *